United States Patent [19]

Bjornson

[11] 4,189,613

[45] Feb. 19, 1980

[54] HYDRODEALKYLATION PROCESS

[75] Inventor: Geir Bjornson, Bartlesville, Okla.

[73] Assignee: Phillips Petroleum Company, Bartlesville, Okla.

[21] Appl. No.: 914,836

[22] Filed: Jun. 12, 1978

[51] Int. Cl.$^2$ ............................................. C07C 39/04
[52] U.S. Cl. ................................................ 568/805
[58] Field of Search .............. 568/805, 736, 740, 763, 568/772; 260/672 R

[56] References Cited

U.S. PATENT DOCUMENTS 2,295,674  9/1942  Meharg et al. ...................... 568/805
2,998,457  8/1961  Paulsen .............................. 568/805

FOREIGN PATENT DOCUMENTS 38-21720 10/1963 Japan ....................................... 568/805

Primary Examiner—Werren B. Lone

[57] ABSTRACT

Substituted aromatic compounds are hydrodealkylated in the presence of hydrogen and a low sodium content chromia-alumina catalyst under conditions of temperature and pressure such that a small amount of nonrecyclable dehydroxylated products such as benzene, toluene and xylenes are obtained.

4 Claims, No Drawings

HYDRODEALKYLATION PROCESS

This invention relates to the dealkylation of alkyl-substituted aromatic compounds. In accordance with another aspect, this invention relates an improved process for the dealkylation of alkyl-substituted aromatic compounds in the presence of a low sodium content chromia-alumina catalyst under dealkylation conditions such that small amounts of nonrecyclable dehydroxylated products are obtained. In accordance with a further aspect, dealkylation of alkyl-substituted aromatic compounds is carried out in the presence of a low sodium content chromia-alumina catalyst at temperatures below about 850° F. so that small amounts of nonrecyclable dehydroxylated products such as benzene, toluene and xylenes, are obtained.

BACKGROUND OF THE INVENTION

As a result of increased coal production to help solve some energy needs, there is an increased coal tar availability from the coke formation process, a coal related industry. Of the various coal tar components, phenol and cresols are the most important with phenol being the most valuable because of its use as a raw material and chemical intermediate in a wide variety of chemical products ranging from heat resistant phenolic resins useful in appliances and electrical components to epoxy resins, medicinals and synthetic fibers. The demand for phenol has, consequently, far outdistanced the ability to supply the material from coal tar and for this reason phenol is now predominantly produced by alternate synthetic methods.

Cresols are used in significantly much smaller quantities for areas such as: ortho cresol for herbicides; meta and para cresols for phenol-formaldehyde resins for molding compounds and adhesives; and tricresylphate production. Any large influx of cresol supply brought about by a potential increase in coal tar products would only serve to over-supply a less demanding market. Cresols are structurally very similar to phenol, differing only in alkyl substitution on an aromatic ring. Dealkylation of these type materials could lead to increased supply of the more valuable phenol and at the same time relieve a potentially oversupplied cresol market.

Accordingly, an object of this invention is to provide an improved process for the hydrodealkylation of aromatic compounds.

A further object of this invention is to provide an improved hydrodealkylation process wherein small amounts of nonrecyclable dehydroxylated products are obtained.

Other objects and aspects, as well as the several advantages of this invention will be apparent to one skilled in the art upon a reading of the specification and appended claims.

According to the invention, an improved process is provided for the hydrodealkylation of aromatic compounds by contacting at least one alkylsubstituted aromatic compound with hydrogen in the presence of a low sodium content chromia-alumina catalyst under dealkylation conditions of temperature and pressure such that small amounts of nonrecyclable dehydroxylated products, such as benzene, toluene and xylenes, are obtained.

More specifically, it has been found that carrying out the hydrodealkylation of substituted aromatic compounds in the presence of a low sodium content chromia-alumina catalyst at temperatures below about 850° F. results in the production of small amounts of nonrecyclable dehydroxylated products and this is contrary to carrying out the process at higher temperatures.

In accordance with another embodiment of the invention, small amounts of nonrecyclable dehydroxylated products such as benzene, toluene and xylenes are obtained when cresols are subjected to hydrodealkylation at temperatures below 850° F. in the presence of a low sodium content chromia-alumina catalyst.

Thus, according to the invention, mixed cresols (ortho, meta, para) are hydrodealkylated to phenols and xylenols under mild reaction conditions when passed over a low sodium-content chromia on alumina catalyst. Utilization of the catalyst herein described results in a small amounts of nonrecyclable products (e.g. benzene, toluene, xylenes) being produced. Therefore, the invention provides a low sodium chromia based catalyst capable of dealkylating alkyl-substituted hydroxyaromatics, such as cresols, in the presence of hydrogen to phenol and xylenols with essentially no formation of nonrecyclable products.

The catalyst used according to the invention is a low sodium content chromia-alumina composite.

The catalyst useful in this invention as well as two control catalyst systems are all commercially available materials based on varying amounts of chromia on alumina. They are activated by heating for 30 to 60 minutes in the presence of hydrogen at slightly above the temperature employed in the hydrodealkylation reaction, this activation being conducted in the same tubular reactor in which the hydrodealkylation takes place. The distinguishing features between the inventive catalyst is the low chromia content and the low sodium content, the latter being the more important. Thus, it is preferred that chromia on alumina catalysts useful in this invention are those having very low sodium content (probably in the form of sodium oxide), less than 0.02 wt. % and with a chromium content between 3 to 55 wt. % on alumina preferably 5 to 25 wt. %.

The inventive catalyst maintains high product selectivity with approximately the same percent conversion when operated for long-time periods such as 16 hours. Operations beyond this time can require catalyst regeneration in which case common methods known in the art such as those employing air/nitrogen mixtures at elevated temperatures are quite satisfactory. Since the inventive catalysts do not significantly coke at the lower operating temperatures described herein, it is preferred that regeneration be conducted by merely passing a hot vaporized hydrocarbon (i.e., toluene) over the catalyst. This operation can be carried out in situ and successfully removes any residual materials.

The aromatic feed subjected to hydrodealkylation according to the invention can be any substituted aromatic compound whether monocyclic or polycyclic having various substituents. More specifically, the feed can be any substituted aromatic having at least one hydroxy group attached to the aromatic ring and having the general formula

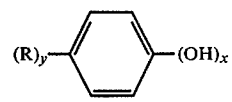

wherein x is 1 to 3 and y is 1 to 5, and the sum of x and y is 2 to 6. R is any hydrocarbyl radical including alkyl, cycloalkyl, alkenyl, or cycloalkenyl radicals having from 1 to 6 carbon atoms. For example, materials to be used, but not limited to, can be cresols (ortho, meta, para-substituted), xylenols (2,3-; 2,4-; 2,5-; 2,6-; 3,4-), trimethylphenols, 4-(2-propenyl)phenol, 2-cyclohexylphenol, 4-cyclohexylphenol, 4-(3-cyclohexenyl)phenol, and the like, and mixtures thereof.

Solvents can be used if so desired and can be, for example, alcohols (e.g., methanol) or aromatic hydrocarbons, preferably benzene.

Hydrogen is co-mixed with the feed and should be in a slight molar excess, preferably about 1.5 moles of hydrogen to 1.0 moles of alkylated hydroxyaromatic (e.g., cresol). Hydrogen helps to prevent unwanted condensation reactions which can lead to coke formation.

The rate of hydrogen-alkyl substituted hydroxy aromatic fed through the reactor should be between about 0.5 and about 10, preferably about 1.0 volumes of feed per volume of catalyst employed. This is referred to as liquid hourly space velocity (LHSV).

The hydrodealkylation conditions employed will be such that a small amount of nonrecyclable dehydroxylated products are obtained and such conditions will include temperatures below about 850° F. and pressures below about 750 psig. In general, the conditions of reactions described herein are as follows:

|  | Broad Range | Preferred Range |
| --- | --- | --- |
| Temperature, F. | 550–850 | 650–800 |
| , C. | 287–454 | 343–426 |
| Pressure, psig | 300–750 | 400–600 |
| , MPa | 2.07–5.17 | 2.76–4.14 |

Any type of reactor, but preferably a tubular reactor of stainless steel (e.g. 316) construction, can be employed. The walls of the reactor should be free of material which will interfere with the catalyzed reaction described herein. The catalyst should be positioned near the middle of the reactor and can be preceeded and followed by a zone of non-catalytic material such as quartz chips. In the specific examples, the catalyst is placed in the reactor chamber with a bed of inert non-catalytic material above and below the catalyst zone and the temperature raised to the reaction temperature while hydrogen gas is passed through the tubular reactor. This serves to dry and activate the catalyst prior to reaction. The run begins by pressuring the pre-heated (50 C.) feed through a filter into a Lapp pump and into the top mixing portion of the reactor zone. A static "o" ring switch, is set about 100 psi, 0.689 MPa above the operating pressure of the system to protect the pump. Hydrogen is pressured through a Moore back-pressure regulator, heated and mixed with the feed just before entering the mixing head. The hydrogen-feed mixture is passed through the reactor and through a steam-jacketed condensor and Moore back-pressure regulator into a chilled receiver. The products can then be analyzed and later separated usually by distillation.

The following examples serve to illustrate the operability of the current invention.

EXAMPLE I

To a stainless steel tubular reactor having the dimensions 2.44 cm (0.960 in) diameter by 70.49 cm (27.75 in) was charged 60 milliliters of the low sodium-content chromia on alumina catalyst and heat activated as herein described. While the temperature was maintained at 371 C. (700 F.) and the pressure at 3.44 MPa (500 psi) an equimolar mixture of ortho, meta and para cresol was fed through the reactor at a rate of about 55 to 60 milliliters per hour (1.0 LHSV), the pressure being maintained by hydrogen which mixes with the feed at a molar ratio of about 1.5 moles of hydrogen to 1.0 moles of cresol. The effluent product was analyzed without further separator with a Bendix ® 2300 chromatograph employing a column comprised of 12 weight percent 6-ringed polyphenyl ether on Chromasorb G, 80–100 mesh size, which had been previously acid washed and dimethylsiliconized. The column was programmed as follows: 100 C. to 190 C. at 30° C./min.; 190 C. to 250 C. at 10° C./min.; and isothermal at 250 C. until complete. Analysis showed a 38.3% conversion with a product distribution of 54% phenol, 2.1% BTX (benzene, toluene, xylenes), 41.8% xylenols and 1.9% unknowns. The run was repeated at 482 C. (900 F.) and gave a 74.1% conversion with a product distribution of 24.0% phenol, 49.6% BTX, 12.9% xylenols and 13.6% unknowns.

EXAMPLE II

The run described in Example I was repeated at 371 C. (700 F.) and at 482 C. (900 F.) except the catalyst used was a higher sodium-content chromia on alumina. Analysis of the products by chromatography as herein described indicated a 10.6% conversion when the run was conducted at 371 C. (700 F.) with a product distribution (selectivity) of 48.7% phenol, 6.7% BTX, and 44.6% xylenols was obtained. At 482 C. (900 F.) the conversion was 58.5% with a product selectivity of 55.8% phenol, 18.4% BTX, 21.3% xylenols and 1.6% unknowns.

EXAMPLE III

The run described in Example I was again repeated at 371 C. (700 F.) and at 482 C. (900 F.) except the catalyst was a higher sodium-content chromia on alumina. Analysis of the products by chromatography as herein described indicated a 1.2% conversion when the run was conducted at 371 C. (700 F.) with a product selectivity of 31.6% phenol, 48.6% BTX, and 19.8% xylenols. At 482 C. (900 F.) the conversion was 54.4% with a product selectivity of 39.2% phenol, 36.5% BTX, 23.4% xylenols and 0.9% unknowns.

The following table summarizes the data herein described.

Table I

| | Catalyst | | Summary (Feed: o,m,p-cresol) | | | | | | |
| --- | --- | --- | --- | --- | --- | --- | --- | --- | --- |
| | Wt. %[a] | Wt. % | Reaction Temperature | | % | % Selectivity | | | |
| | Cr | Na | °C. | °F. | Conversion | Phenol | BTX[b] | Xylenols | Unknowns |
| Example I | 19 | <0.01 | 371 | 700 | 38.3 | 54.2 | 2.1 | 41.8 | 1.9 |
| | | | 482 | 900 | 74.1 | 24.0 | 49.6 | 12.9 | 13.6 |

Table I-continued

Summary
(Feed: o,m,p-cresol)

| | Catalyst | | Reaction Temperature | | % Conversion | % Selectivity | | | |
|---|---|---|---|---|---|---|---|---|---|
| | Wt. %[a] Cr | Wt. % Na | °C. | °F. | | Phenol | BTX[b] | Xylenols | Unknowns |
| Example II | 23 | 0.06 | 371 | 700 | 10.6 | 48.7 | 6.7 | 44.6 | — |
| | | | 482 | 900 | 58.5 | 55.8 | 18.4 | 21.3 | 1.6 |
| Example III | 20–25 | 0.07 | 371 | 700 | 1.2 | 31.6 | 48.6 | 19.8 | — |
| | | | 482 | 900 | 54.4 | 39.2 | 36.5 | 23.4 | 0.9 |

[a]Approximate
[b]Benzene, toluene, xylenes

The results shown in the summary, Table I, indicate the least amount of nonrecyclable products, BTX, are obtained with good conversion when a low sodium content chromia-on-alumina catalyst is used to hydrodealkylate a feed comprised of an equimolar mixture of o-, m-, and p-cresol in the presence of hydrogen, Example I. In addition, this low sodium content chromia catalyst has an optimum operating temperature about 110° C. below that required for two other similar chromia-on-alumina catalysts.

The two similar catalyst used as controls contain about 20 percent more chromia than the catalyst of the invention and a significantly greater amount of sodium, probably in the form of sodium oxide.

I claim:

1. A process for the hydrodealkylation of monocyclic aromatic compounds under conditions such that small amounts of nonrecyclable dehydroxylated monocyclic products are formed which comprises contacting at least one hydroxy-substituted aromatic hydrocarbon having the general formula

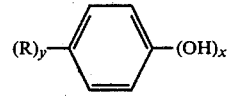

wherein x is 1 to 3 and y is 1 to 5 and the sum of x and y is 2 to 6, and R is a hydrocarbyl radical having from 1 to 6 carbon atoms with hydrogen in the presence of a catalyst consisting essentially of a low sodium compound content chromia-alumina composite containing less than 0.02 wt. % sodium at a temperature below about 850° F. and a pressure below about 750 psig which conditions are conducive to the formation of large amounts of phenols and small amounts of nonrecyclable dehydroxylated products such as benzene, toluene, xylenes, and the like.

2. A process according to claim 1 wherein said catalyst contains from about 5 to about 25 wt. % chromia and less than 0.02 wt.% sodium and the temperature of contact is in the range of about 650°–800° F. (343°–426° C.) and a pressure of about 400–600 psig.

3. A process according to claim 1 wherein said hydroxy-substituted aromatic feed comprises at least one of ortho, meta and para cresols and the temperature of contacting is in the range of about 650°–800° F. (343°–426° C.) and a pressure in the range of about 400–600 psig and the product comprises phenols and xylenols and small amounts of benzene, toluene and xylenes.

4. A process according to claim 3 wherein said feed is a mixture of ortho, meta and para cresols.

* * * * *